United States Patent [19]
Bealing et al.

[11] Patent Number: 5,990,199
[45] Date of Patent: Nov. 23, 1999

[54] INDICATOR INK COMPOSITIONS

[75] Inventors: John R. Bealing, Smyrna; Joel R. Gorski, Marietta, both of Ga.

[73] Assignee: North American Science Associates, Inc., Northwood, Ohio

[21] Appl. No.: 08/423,452

[22] Filed: Apr. 19, 1995

[51] Int. Cl.$^6$ .................................................. C09D 11/10
[52] U.S. Cl. .................... 523/161; 524/508; 524/509; 524/510; 260/DIG. 38; 523/208; 106/31.13; 106/31.18; 106/31.27
[58] Field of Search ...................... 523/164, 208; 260/DIG. 38; 524/508, 509, 510; 160/20 R, 22 R, 31.13, 31.18, 31.27

[56] References Cited

U.S. PATENT DOCUMENTS

| | | | |
|---|---|---|---|
| 34,515 | 1/1862 | Foley | 374/160 |
| 2,606,654 | 8/1952 | Davis et al. | 206/459.1 |
| 3,290,499 | 12/1966 | Vale et al. | 250/474.1 |
| 3,667,916 | 6/1972 | Sliva et al. | 436/1 |
| 3,691,380 | 9/1972 | Hübner et al. | 250/474.1 |
| 3,743,846 | 7/1973 | Matsumoto et al. | 250/474.1 |
| 3,932,134 | 1/1976 | Fang et al. | 422/119 |
| 4,001,587 | 1/1977 | Panchenkov et al. | 250/474.1 |
| 4,015,937 | 4/1977 | Miyamoto et al. | 436/1 |
| 4,021,252 | 5/1977 | Banczak et al. | 106/30 R |
| 4,024,096 | 5/1977 | Wachtel | 523/160 |
| 4,038,873 | 8/1977 | Kimmel | 374/102 |
| 4,042,545 | 8/1977 | Défago et al. | 106/22 C |
| 4,045,397 | 8/1977 | Parkinson | 524/262 |
| 4,155,895 | 5/1979 | Rohowetz et al. | 524/89 |
| 4,165,399 | 8/1979 | Germonprez | 427/264 |
| 4,166,044 | 8/1979 | Germonprez et al. | 252/488.1 |
| 4,179,397 | 12/1979 | Rohowetz et al. | 252/408.1 |
| 4,188,437 | 2/1980 | Rohowetz | 428/199 |
| 4,298,569 | 11/1981 | Read | 422/27 |
| 4,421,560 | 12/1983 | Kito et al. | 106/21 E |
| 4,448,548 | 5/1984 | Foley | 374/160 |
| 4,514,361 | 4/1985 | Hirsch | 422/26 |
| 4,579,670 | 4/1986 | Payne | 507/211 |
| 5,057,433 | 10/1991 | Douglas | 436/1 |
| 5,064,576 | 11/1991 | Suto | 556/37 |
| 5,084,623 | 1/1992 | Lewis et al. | 250/474.1 |
| 5,087,659 | 2/1992 | Fujisawa | 524/594 |
| 5,158,363 | 10/1992 | Speelman et al. | 374/102 |
| 5,258,065 | 11/1993 | Fujisawa | 106/22 B |
| 5,340,537 | 8/1994 | Barrett | 422/26 |

FOREIGN PATENT DOCUMENTS

| | | |
|---|---|---|
| 1271393 | 7/1918 | Netherlands . |
| 920689 | 10/1969 | United Kingdom . |
| 2055393 | 3/1981 | United Kingdom . |

OTHER PUBLICATIONS

"Chemical Abstracts," Journal: *Chemical Abstract Service*, vol. 103, p. 84, Oct. 7, 1985. 106435f.

*Primary Examiner*—Vasu Jagannathan
*Assistant Examiner*—John J. Guarviello
*Attorney, Agent, or Firm*—James Remenick; Baker & Botts, LLC

[57] ABSTRACT

The invention relates to indicator ink compositions that contain a water-based dispersion of a phenol-formaldehyde resin, at least one colorant and an amine-terminated catalyst. These indicator ink compositions are fixed to a surface, such as by drying, and respond to specific conditions of time, temperature, humidity, pressure and the presence or absence of certain chemicals by changing color. Compositions provide a means for detecting exposure to a predetermined condition and can be fixed or otherwise attached to nearly any article or designed into patterns on materials. Exposure of the indicator ink to the specific condition, the indicator ink provides a permanent detectable record of the event. Further, by varying the amount of amine-terminated catalyst in the formulation, the specific conditions at which the indicator composition will change color can be altered. Such compositions are specifically useful for determining the effectiveness of a sterilization process.

23 Claims, No Drawings

INDICATOR INK COMPOSITIONS

BACKGROUND

1. Field of the Invention

The invention relates to ink compositions which provide a detectable indication of conditions involving time, temperature, pressure, energy or the presence or absence of certain chemicals. These compositions are useful in industry and manufacturing for detecting environmental conditions and in medicine for determining the effectiveness of sterilization processes.

2. Background of the Invention

In many areas of manufacturing, analysis and research, and especially in the field of medical research and testing, exposure to sterilants is required to accomplish specific objectives such as curing a component, rendering a device sterile or determining how a material withstands exposure to a sterilant or to a sterilizing environment. Sterilization processes to which materials can be exposed include, inter alia, gamma radiation, ethylene oxide, E-beam, steam, vapor phase hydrogen peroxide, ultraviolet light, dry heat, peracetic acid, gas plasma and steam-formaldehyde.

Sterilization is generally defined as the process of completely destroying all viable microorganisms including organisms such as viruses and spores. Considering the risks associated with improper sterilization, it is always beneficial to monitor the effectiveness of material sterilization. Standard practice is to include a sterility indicator with the articles to be sterilized. The use of sterility indicators allows for a direct and sensitive approach to assess the lethality of the process. The typical sterility indicator is a packaged assembly of components which is placed into the sterilizing environment with the articles to be sterilized. These components are specifically affected by one or more parameters of the sterilization process and analyzed after completion of the procedure. These and other conventional indicators are described in U.S. Pat. Nos. 2,606,654, 4,596,773 and 4,717,661, which are hereby specifically incorporated by reference as are all U.S. patent documents cited herein.

There are two general types of sterility indicators, biological indicators and chemical indicators. Biological indicators, as their name implies, contain a biologically-derived test material. A standard type of biological sterility indicator, for example, as described in U.S. Pat. No. 4,732,850, contains a known quantity of test microbial spores. The indicator is placed into the sterilization chamber and exposed to the sterilization process along with the objects to be sterilized. Test microorganisms from the exposed indicator, such as *Bacillus stearothennophilus* or *B. subtilis* spores, are incubated in a growth medium for a specified period of time under conditions which favor microbial proliferation. The incubation medium is then examined for signs of growth which may be determined by the presence or absence of metabolic products. Typically, growth is detected by a pH change of the incubation medium. A low pH is positive for growth and indicates that the sterilization process was insufficient to destroy all of the microorganisms. These and other variations of the biological sterility indicator are disclosed in U.S. Pat. Nos. 3,239,429, 3,440,144, 3,661,717, 4,596,773, 4,717,661, 4,732,850, 4,741,437, 4,743,537, 4,885,253 and 5,167,923.

A major drawback of biological sterility indicators is the time delay in obtaining results of the test. Indicators typically require incubation for periods of time which, in the case of spore containing indicators, can be several days. To help ensure complete safety, items which were subjected to the sterilization process should not be used during this period. The practitioner should wait until the results of the viability test have been determined, and if proper sterilization conditions were not met, wait even longer for the materials to be re-sterilized and re-tested.

Chemical indicators contain an analyzable chemical and provide a more general indication of exposure to a sterilization process by detecting or measuring one or more of the parameters of the process. Most chemical indicators provide a visual indication of exposure to the sterilization process and contain, for example, a thermotropic ink. The ink can be fixed by, for example, printing directly onto the article to be sterilized or onto a wrapping or attachment to the target article. The article and the chemical indicator ink composition are then exposed to the sterilization process and upon completion, the indicator provides an indication of exposure to or a measure of the effectiveness of the process.

The most widely used chemical indicators contain inks which change color in response to predetermined states or conditions of local environment such as would occur during sterilization. For example, as described in U.S. Pat. No. 3,667,916, a chemical compound such as silver nitrate will darken upon exposure to heat, high humidity and/or the presence of ethylene oxide. An indicator device containing this compound, and exposed to a steam or ethylene oxide sterilization process, darkens in color. Substantial darkening provides an indication that the sterilization process has been encountered. No post-sterilization incubation period is required and, thus, results can be determined immediately.

As chemical indicators are designed to react to the critical parameters associated with a particular sterilization process there are at least as many variations of chemical indicator compositions as there are sterilization processes. For example, a steam sterilization process indicator utilizes an indicator composition which determines that a set temperature, pressure, time or combination of these events have been achieved. With a dry heat sterilization process, the chemical indicator provides an indication that a certain predetermined temperature had been reached for a given period of time. For an ethylene oxide sterilization process, the chemical indicator provides an indication that a predetermined gas concentration existed in the sterilization chamber. Failure to elicit a detectable color change demonstrates that one or more parameters associated with that particular sterilization process were not achieved and immediately warns the user that a problem may exist.

A wide variety of chemical indicators have been developed that rely on a color change to determine the sufficiency of the sterilization process. For example, Rohowetz et al. (U.S. Pat. No. 4,179,397) is directed to organic solvent-based ink compositions used as sterilization or pasteurization indicators. An ink composition is considered to be organic solvent-based if they are greater than 25% organic solvent by weight. These inks comprise a solution of binder resin such as a phenol-formaldehyde or resorcinol-formaldehyde class of phenolic resin chemicals, a thermotropic dye that undergoes a color change at about 215° F. (101° C.), and an organic solvent blend consisting essentially of a lower aliphatic monohydric alcohol at between about 25% to about 100%. These resins are alcohol-based and have a molecular weight in range of between about 1,300 to about 10,000.

Rohowetz et al. (U.S. Pat. No. 4,155,895) is directed to thermotropic inks which comprise a binder resin component, an alcohol solvent and a colorant. The colorant is a dye and may be classified as a substituted phenazine or diazotization product of a safranine forming Janus Green B, Janus Blue, Indoine Blue, Janus Black, Copying Black SK and Copying Black 1059/1527. Compositions are stated to produce a detectable color change upon exposure to temperatures of at least about 215° F. for periods of time ranging from 2 to 90 minutes.

Germonprez et al. (U.S. Pat. No. 4,166,044) is directed to binderless ink compositions for use in jet printing operations on polymeric resin surfaces to form images that are resistant to abrasion, and which respond to steam sterilization or pasteurization. The inks utilized change color upon exposure to steam at elevated temperatures.

Banczak et al. (U.S. Pat. No. 4,021,252) is directed to ink compositions suitable for ink jet printing on metal surfaces. The compositions comprise a colorant comprised of a shellac and a dye such as auramine, chrysoidine, crystal violet or another basic dye, and an alcohol-water solvent blend to lower the surface tension of the ink for printing on the metal surface of cans. Compositions may also contain electrolytes to lower the specific resistivity of the ink, often necessary for printing on metal surfaces.

Rohowetz (U.S. Pat. No. 4,188,437) is directed to an adhesive tape which changes color in the presence of water or steam at elevated temperatures. The tape comprises a polymeric base layer having at least one surface of a thermotropic ink. The ink comprises a binder resin in a solvent blend consisting essentially of a lower alcohol or alcohol mixed with an oxygenated organic compound such as aliphatic or cyclic ketones, esters or ethers, and a solution of colorants and surfactants.

These thermotropic indicator inks all contain organic solvents such as the volatile organic compounds (VOC) methyl ethyl ketone, toluene and dimethyl sulfoxide, and metallic salts such as carbonates of lead and copper. Color development is a consequence of a reaction of the metallic salt with a sulfur component resulting in the generation of a black metallic sulfide.

These types of conventional indicators have a number of problems as a result of their formulations. First, there is a limited development of color change. As black is the most prevalent signal color, it is often difficult to distinguish shadings. Second, the color change emits an offensive odor in compositions containing metallic sulfides. Third, compositions typically reach endpoint or, in other words, maximal color change immediately upon exposure to the elevated levels of temperature and humidity. Therefore, a graded response to increasing exposure cannot be easily achieved. There are also important environmental hazards associated with the manufacturing, handling, transportation, disposal and landfill of heavy metals such as lead. These hazards are present both before and after disposal such as in manufacturing and use by patients and health care workers.

SUMMARY OF THE INVENTION

The present invention overcomes the problems and disadvantages associated with current strategies and designs and provides indicator ink compositions and sterility indicators containing these compositions which can be useful for detecting local environmental conditions of temperature, humidity, pressure and the presence or absence of specific chemicals as may occur in a sterilization process.

One embodiment of the invention is directed to indicator ink compositions containing a water-based dispersion of phenol-formaldehyde resin, at least one colorant and an amine terminated catalyst. These indicator ink compositions may be thermotropic and cross-link, thereby becoming detectable, upon exposure to predetermined conditions of temperature, pressure or humidity, or the presence or absence of specific chemicals. Compositions can be used to detect or monitor the effectiveness of a sterilization process or to detect the occurrence of one or more predetermined environmental conditions.

Another embodiment of the invention is directed to methods for determining the effectiveness of sterilization processes. An indicator ink composition, containing a phenol-formaldehyde resin dispersion in water, at least one colorant and an amine-terminated catalyst, is subjected to the sterilization process along with an article to be sterilized. The ink composition may be housed separately or attached directly or indirectly to the article. Upon completion of the process, the indicator ink is observed for a detectable change in color. Sterilization processes which can be monitored by these methods include steam, dry heat, ethylene oxide, steam formaldehyde, vapor phase hydrogen peroxide, peracetic acid and gas plasma.

Another embodiment of the invention is directed to articles to which are fixed indicator ink compositions that contain a water-based dispersion containing phenol-formaldehyde resin, at least one colorant, and an amine-terminated catalyst. Articles may be reusable materials such as medical instruments which can be sterilized or disposable materials which are used once and discarded. Monitoring the sterilization process assures the user that the articles have been properly subjected to the parameters required for sterilization.

Another embodiment of the invention is directed to sterility indicators. Sterility indicators can be used to monitor the effectiveness of a sterilization process and comprise a substrate having an indicator ink composition affixed thereto. The indicator ink composition is comprised of a dispersion of phenol-formaldehyde resin in water, at least one colorant and an amine-terminated catalyst. The substrate may be a container which is penetrable by the exterior environment, having the ink composition affixed to an inner surface thereof by drying. A color change of the ink can be visualized through the container.

Another embodiment of the invention is directed to methods for detecting predetermined conditions such as specific temperatures, pressures or humidities, or the presence or absence of specific chemicals. An indicator ink composition containing a phenol-formaldehyde resin dispersion in water, at least one colorant, and an amine-terminated catalyst is fixed to an article. The article is examined to detect a color change of the ink which indicates that the article has been exposed to the predetermined environmental conditions. Such methods are useful for monitoring conditions during the manufacture and transportation or storage of such goods as foods, pharmaceuticals, chemicals, biologically-derived products or agricultural products. Such methods can also be used to determine if pasteurizing conditions exist or if effective pasteurization of a product has been achieved.

Other embodiments and advantages of the invention are set forth, in part, in the description which follows and, in part, will be obvious from this description and may be learned from the practice of the invention.

DESCRIPTION OF THE INVENTION

As embodied and broadly described herein, the present invention is directed to indicator ink compositions, to articles which can be marked with the ink compositions and to methods for using the ink compositions, such as, for example, in determining the exposure to a sterilization process.

Sterilization monitoring involves detecting or measuring the exposure of an article, which may be a reusable surgical instrument or a disposable device, to specific conditions or states which occur during the sterilization process. Conventional chemical sterility indicators contain organic solvents such as alcohols, phenolic compounds or other relatively volatile organic chemicals which are fairly flammable and often toxic. There remain significant risks and costs to the manufacturer. In addition, these compositions contain heavy metals and sulfur compounds which can be harmful to the environment.

The present invention provides an indicator ink composition which possesses none of these hazards. Indicator ink compositions of the present invention are water-based dispersions requiring little if any organic solvents during manufacture. Heavy metals, sulfur compounds and volatile organic compounds are not required and, consequently, manufacturing and disposal problems typically associated with these components are minimized or absent. These ink compositions have the additional advantage that sensitivity to the specific parameter being measured can be adjusted by increasing or decreasing the concentrations of one or more of the components of the composition. Further, and in contrast to conventional organic solvents, purified water as a solvent provides a less-volatile medium which significantly reduces the costs and the hazards associated with product manufacturing, use and disposal. Resulting compositions have a lower VOC content and greater stability in comparison to conventional compositions.

One embodiment of the invention is directed to an indicator ink composition which comprises a water-based dispersion of a resinous formaldehyde binder such as phenol-formaldehyde resin, at least one colorant and an amine-terminated catalyst. In combination, these components elicit a detectable change when exposed to one or more parameters associated with a sterilization process. Such parameters include, but are not limited to, conditions such as temperatures from about 0° C. and below to about 260° C. and above, pressures greater than atmospheric pressure, times from seconds to minutes or hours, or even years depending on associated conditions, humidity levels from the absence of detectable water to saturating conditions, radiation exposure greater than about one kGy, the measurable presence or absence of certain chemicals such as ethylene oxide, formaldehyde, peracetic acid or hydrogen peroxide, or combinations of these conditions. As ink sensitivity can be adjusted, the set of parameters at which the ink will detectably change can vary widely. Sensitivity can be set to exact conditions which may be known or empirically determined.

Phenol-formaldehyde resin dispersions which can be used in indicator ink compositions of the present invention can be classified as (1) alcohol-soluble resole resins, (2) colloid-protected water-borne dispersions of phenol-formaldehyde resins based on para tertiary butyl phenol, or (3) oil-modified phenol-formaldehyde varnishes. Preferably, the resin component is a colloid-protected water-borne dispersion of a phenol-formaldehyde resin which is infinitely dilutable with water.

Resins may be coated with various polymeric materials including but not limited to polyvinyl alcohol or acrylic. Coatings serve to further stabilize the resin and provide increased resistance to the extremes of heat which occur with many types of sterilization processes. Preferably, resins are coated by cooking the uncoated base substances in the presence of a drying oil. Phenol-formaldehyde resins can be cooked to a point well beyond the gelation stage without any significant destruction to the resin base.

The greater stability of the compositions is due, at least partly, to the slower evaporation rate of purified water as compared with the evaporation rate of organic solvents used in other indicator compositions. The resulting dispersion has a molecular weight of less than 1000 and is diluted with water and a small amount of coalescent solvent, such as butyl cellosolve. Some examples of resins which may be used include Bakelite BKUA-2370 (Georgia Pacific), HRJ1057 and HRJ11935 (Schenectady International).

Colorants of the indicator ink compositions can be dyes or combination of dyes which provide a visible and preferably permanent color change when exposed to the conditions of sterilization. The dyes of choice are soluble in the composition and compatible with the various components. Suitable dyes can be divided into reactive dyes, extractable dyes and non-extractable dyes. The reactive and extractable dyes may be used either alone or in combination with one another or in combination with non-extractable dyes.

Colorants of the composition vary in amounts from about 0.5% to about 5% by weight. If a combination of dyes is used, the ratio of extractable to non-extractable dye is between 1:1 and 4:1, preferably between 2:1 and 3:1 and more preferably about 2:1. Preferably, the indicator inks comprise reactive dyes such as, for example, substituted phenazines or diazotized products of Safranine O. Suitable reactive dyes include Janus Green B (colour index ("CI") #111050), Janus Blue (CI #12211), Janus Black (CI #11825), Copying Black SK (CI #11957) and Copying Black 1059/1427 (CI #11090). Quinine Oximes may also be useful as reactive dyes, examples include 2,6-Dinlitrophenol and Maritus Yellow (CI #10315).

Classes of extractable dyes suitable for use include, among others, aniline dyes or sodium sulfonate salts of triphenyl methane dyes. Specific examples of dyes of these classes include Aniline Blue (CI #42755), Light Green SF (CI #42095), FD&C Green #1 and Acid Blue #7. Extractable dyes can also come from sodium sulfonate salts of induline such as Acid Blue #20.

Classes of non-extractable dyes which may be used include, among others, phenylsafranine dyes. Examples of such dyes are Safranine O, Rhoduline Violet (CI #44045) and Methyl Red (CI #13020). Safranine O as the non-extractable dye in combination with extractable dyes such as Aniline Blue or Light Green SF yields good results that can be easily detected. Such a combination results in an initial color of dark blue, which undergoes transition to a signal color of pink to red.

Phenol-formaldehyde resins cross-link at elevated temperatures, generally above 149° C. This cross-linking causes the indicator composition to undergo a permanent color change. The variables that determine the manner in which the phenol-formaldehyde resin and dyes interact include: for a steam sterilization process; temperature, pressure, saturated steam content and exposure time: and for an ethylene oxide sterilization process: temperature, humidity, ethylene oxide gas concentration and exposure time.

Indicator ink compositions contain an amine-terminated polyamide curing agent as a cross-linking agent for the phenol-formaldehyde resin dispersion. The use of an amine-terminated polyamide curing agent in conjunction with a phenol-formaldehyde resin was generally thought to be difficult if not impossible because most polyamide curing agents are used at a 1:2 ratio in two pack solid epoxy systems that, when mixed, have relatively short pot lives of about 3 to about 4 hours.

In addition, a polyamide curing agent in conjunction with a phenol-formaldehyde resin allows for compositions to be formulated to cross-link at a time after the critical sterilization parameters have been achieved thereby modulating the sensitivity of the indicators. Adjusting the concentration of polyamide curing agent in relation to the concentration of phenol-formaldehyde resin will alter the sterilization parameters at which the resulting indicator changes color. The greater the concentration of polyamide curing agent, the more sensitive the resulting indicator composition. The smaller the concentration of polyamide curing agent, the less sensitive the resulting indicator composition. The amine-terminated polyamide curing agent is a condensation product manufactured by pre-condensing a di-primary amine with a dimer acid. Homopolymerization occurs between the phenol-formaldehyde methylols and the secondary hydrogens of the amine-terminated polyamide curing agent component. The polyamide curing agent should have an amine value between about 100 to about 400. Some suitable examples of polyamide curing agents include UNIREZ E-3358 (Union Camp), Epicure 3140 and Epicure 3100-XY-60 (Shell Resins).

Indicator compositions may also include various conventional additives such as electrolytes, defoaming agents, dispersing agents, drying agents, opacifiers, rheology modifiers, slip additives, surfactants and viscosity increasing agents. These additives are generally added in amounts between 0.1% and 5% by weight of the total dispersion and are compatible with the different compositions and coatings.

Preferably, indicator compositions provide a permanent color change when subjected to predetermined or local environmental conditions. Predetermined means that the particular states of temperature, pressure, humidity, radiation, chemical concentration or combination of conditions at which the dye will change color can be preset. The polyamide curing agent cross-links the phenol-formaldehyde resin when exposed to a sterilization process. Specifically, the polyamide curing agent reacts with the hydroxy methylol groups on the phenol-formaldehyde resin thereby creating reactive sites for condensation. The inclusion of a greater concentration of the polyamide curing agent increases the sensitivity and reactivity of the composition.

The reaction between the polyamide curing agent and the phenol-formaldehyde resin component causes the release of water at condensation sites. During steam sterilization, this water is super heated within the matrix of the thin film and cleaves the azo bond of the diazotized dye stuff resulting in creation of a moiety of Safranine O which gives rise to the color change in the indicator composition.

For indicator compositions with reactive dyes to function properly, the entire composition is usually balanced for optimal performance and stability. These compositions are stable at room temperature and stable for long runs on a printing press. An excess of the polyamide curing agent will cause the indicator composition to overreact and discolor the printed indicator. This produces an erroneous transition in color not representative of proper exposure of the indicator composition to sterilization conditions.

For indicator compositions using extractable dyes, the associated extraction or leaching step does not occur until the indicator composition has been exposed to temperatures above about 50° C. (120° F.). Extraction of the dye occurs during the cross linking and condensation of the phenol-formaldehyde resin component and should be complete prior to the stage at which the phenol-formaldehyde component crosslinks fully or the extractable dye will not leach out.

These compositions are contact printable and extremely stable at room temperature for greater than six months and preferably for greater than one year. Compositions may be incorporated into inks, paints and other formulations that may be applied in a variety of manners such as flexographic, roto-gravure, roll coating, lithographic, offset, silkscreen and the like, and to a variety of substrates such as tapes, labels, bags, pouches and cards suitable for use as sterilization indicators. Compositions may also be applied in various shapes, sizes and thicknesses based upon a desired outcome.

Another embodiment of the invention is directed to an article comprising a surface to which has been fixed a thermotropic ink composition containing a water-based dispersion of phenol-formaldehyde resin, at least one colorant and an amine-terminated catalyst. The article may be reusable or disposable such as plastics for tissue culture. Articles may be composed of plastic, ceramic, glass, paper, cardboard, wood, metal or combination thereof such as laminates. Specifically useful articles are packaging materials such as paper or plastic which can be used to wrap objects to be sterilized. The article may be, for example, an adhesive tape which is attached to a container such as a can, bottle, bowl, box, crate, pouch or bag.

The indicator ink composition may also be fixed to a surface of the article by, for example, drying to a surface of the article with heat or moving air, or a surface of a different article attached to the first article. Preferably, the phenol-formaldehyde resin of the composition is stabilized with a non-ionic colloid. The composition comprises one or more dyes selected from the group consisting of reactive dyes, extractable dyes and non-extractable dyes. The amine-terminated catalyst is present in an amount between about 0.5% to about 13% of the total weight of the composition. Preferably, the amine-terminated catalyst is present in an amount between about 8% to about 11%, and more preferably at about 10%.

Another embodiment of the invention is directed to a sterility indicator, for indicating exposure to a sterilant or sterilization process, comprising a substrate having affixed thereto an indicator ink composition containing a dispersion of phenol-formaldehyde resin in water, at least one colorant and an amine-terminated catalyst. The indicator ink composition can be affixed to the substrate by drying the water of the composition to create a coating or spot on the article. The coating may be formed into shapes such as stripes or letters such as "AUTOCLAVED", "EXPOSED" or "STERILIZED" to indicate to the user that the article has been exposed to the sterilant or sterilization process. Further, the sterility indicator may be combined with a biological indicator to create an indicator with the advantages of both types of devices. Biological indicators may comprise spores, bacteria or enzymes.

Another embodiment of the invention is directed to a method for determining the effectiveness of a sterilization process. An indicator ink composition is fixed or otherwise attached to an article and the article sterilized in, for example, an autoclave. The indicator ink of the sterilized article is examined for evidence of a detectable change in the ink such as a color change. Compositions may be fixed by drying to a surface of a sterility indicator or fixed to the objects to be sterilized. Sterilization processes with which sterility indicators containing indicator ink compositions of the invention may be used include, inter alia, ethylene oxide sterilization processes, dry heat sterilization processes, steam formaldehyde, vapor-phase hydrogen peroxide, peracetic acid, gas plasma and steam heat sterilization processes. To provide the maximum flexibility to the indicator composition the amount of amine-terminated catalyst in the composition alters the condition which causes the ink to detectably change. Sterilization processes which can pose vastly different sterilization parameters are all testable according to the invention as the ink can be modified to adjust reactivity patterns.

Another embodiment of the invention is directed to a method for detecting a local environmental condition. An article is marked with an indicator ink composition. Marking can be performed by fixing the indicator ink composition directly to the article or to an object attached to the article. After a period of time, periodically as a quality check or after exposure to an uncertain set of conditions such as may occur in transportation, the indicator ink of the marked article is examined for a predetermined detectable change. That change signals to a monitor, which may be a person or an automated detector device, that a predetermined event has or has not occurred. Preferable color changes are from a shade of blue or green to a shade of red or violet, or from a light color such as yellow, tan or white to a dark color such as orange, black or gray. A detectable change can be observed visually and indicates that the article had been subjected to, for example, appropriate pasteurizing conditions, and thus pasteurized, a harmful temperature change or storage for an extended period of time.

Automated devices used to detect such changes may include computer and computer software and may be integrated into the machinery of manufacturing, packaging, transportation or storage. The article may be one or more samples from an assembly line such as used in packaging food products, agricultural products, perishable chemicals, electrical devices, biologically-derived substances or pharmaceuticals. Typical food products which need to be monitored include beverages such as soda, wine and beer, dried and fresh fruits and vegetables, dairy foods and meats and poultry. Using the methods of the invention, harmful conditions that can occur during manufacture, transportation or storage can be easily determined.

The following experiments are offered to illustrate embodiments of the invention, and should not be viewed as limiting the scope of the invention.

EXAMPLES

Example 1

Performance Specifications

Indicator ink compositions can be altered to react in response to a desired condition or set of conditions. Compositions were tested against different performance specifications. Performance specification chosen for presentation is the International Standards Organization (ISO) guidelines for Chemical Indicators (11140-1). Exposures occurred using a Biological Indicator Evaluator Resistometer (BIER) vessel to assure critical control of sterilization conditions.

For steam sterilization process indicators there are three performance specifications defined as follows:

Dry Heat Dwell—After exposure to a previously stabilized condition of dry heat at 140° C.±2° C. for 30 minutes±1 minute, the indicator shall show either no change or shall show a change that is markedly different from the change occurring after exposure to a steam sterilization process, Lower Window—The endpoint indicating exposure to a steam sterilization process shall not occur until the indicator has been exposed to saturated steam for not less than 3 minutes at 121° C. +3/−0 K. (i.e., 3 degrees higher or 0 degrees lower) or 30 seconds at 134° C. +3/−0 K, and Upper Window—The indicator shall provide clear visual evidence of exposure to the process after being subjected to dry saturated steam for not more than 10 minutes at 121° C. +3/−0 K, and not more than 2 minutes at 134° C. +3/−0 K.

For ethylene oxide sterilization process indicators there are three performance specifications defined as follows:

Humidity Dwell—After exposure to 60° C.±2 K at greater than 85% RH for not less than 90 minutes, the indicator shall show either no change or a change that is markedly different from the change occurring after exposure to the ethylene oxide sterilization process, Lower Window—The endpoint indicating exposure to an ethylene oxide sterilization process shall not occur until the indicator has been exposed to 600±30 mg/l ethylene oxide and 60±10% RH at 30° C.±1 K for not less than 5 minutes, and Upper Window—The endpoint indicating exposure to an ethylene oxide sterilization process shall occur when the indicator has been exposed to 600±30 mg/l ethylene oxide and 60±10% RH at 30° C.±1 K for a period not exceeding 30 minutes.

While there are a variety of classes of chemical indicators that the ISO document defines, the above class of process indicators is used only for purposes of illustrating the flexibility of indicator compositions in meeting a wide variety of performance specifications (such as ISO and AAMI—Association for Advancement of Medical Instrumentation).

Example 2

Indicator Ink Composition Formulation A

An indicator ink composition was formulated by mixing the following ingredients into a dispersion;

| 43.5% | BKUA 2370 |
| 37.8% | Purified Water |
| 13.1% | Titanium Dioxide |
| 3.2% | E-3358 Polyamide Curing Agent |
| 1.1% | Sodium Laurel Sulfate |
| 1.0% | Janus Green B |
| 0.3% | Thickener (cellulosic) |

The fluid ink dispersion was printed using a flexographic printing press onto coated and uncoated lithographic paper stock, onto coated and uncoated clear polyester and onto a pharmaceutical lithographic substrate. The composition was thixotropic in nature with a Brookfield viscosity of 3,000 cps and presented an acceptable dry time. Indicators printed using this formulation, when exposed to the ISO parameters defined for the Dry Heat Dwell, underwent transition in color from the initial blue green color to a shade of brown. When the composition was exposed to the parameters associated with the Lower Window it did not change from the initial blue green color. Indicators printed using this formulation, when exposed to the ISO parameters defined for the Upper Window, also did not change from the initial blue green color. Indicators printed using compositions of this formulation and exposed to the ISO parameters defined for the Upper Window, but for a length of 45 minutes, underwent transition from the initial blue green color to the violet signal color.

Example 3

Indicator Ink Composition Formulation B

An indicator ink composition was formulated by mixing the following ingredients into a dispersion;

| | |
|---|---|
| 41.0% | BKUA-2370 |
| 36.2% | Purified Water |
| 10.2% | L-3358 Polyamide Curing Agent |
| 10.1% | Titanium Dioxide |
| 1.2% | Sodium Laurel Sulfate |
| 1.0% | Janus Green B |
| 0.3% | Thickener (cellulosic) |

The above formulation was printed in the same way on the same substrates as was the composition of Example 2. Indicators printed using the composition of this formulation performed exactly as described above for the Dry Heat Dwell and the Lower Window, but when exposed to the conditions specified in ISO for the Upper Window the indicators underwent transition from an initial blue green color to violet signal color.

The performance of formulations A and B demonstrate that an indicator's response to a given sterilization cycle can be controlled by altering the concentration of the polyamide curing agent.

Example 4

Indicator Ink Composition Formulation C

An indicator ink composition was formulated by mixing the following ingredients into a dispersion;

| | |
|---|---|
| 42.7% | ULTREX 49 Soya Based Varnish |
| 18.0% | ULTREX 33 Soya Based Varnish |
| 13.0% | Titanium Dioxide |
| 9.2% | Ethanol |
| 9.8% | Magie 47 Lithographic Oil |
| 5.0% | E-3358 PolyaMide Curing Agent |
| 1.0% | Cobalt Octoate (drier) |
| 0.6% | Janus Green B |
| 0.7% | Manganese Octoate (drier) |

The above composition resulted in a paste and was intended for use with an offset letter press and was printed onto both a coated and an uncoated lithographic paper stock, onto a coated and an uncoated clear polyester and onto a pharmaceutical lithographic substrate. When exposed to the three ISO cycles for steam process indicators, the indicators printed using this formulation performed exactly as those of Example 2. When the two phenol-formaldehyde resins were decreased by 5% total (or 2.5% each) and the polyamide curing agent increased by 5% the resulting composition was printed onto the same substrates and exposed to the three ISO BIER vessel cycles. These altered indicators satisfied the requirements set forth by all three ISO specifications for steam sterilization process indicators.

Indicator ink compositions may be formulated for the offset letter press. The inclusion of the phenol-formaldehyde resin component, polyamide curing agent, and dye into an oil based varnish in no way diminishes the performance of the indicator composition in the pot, on the press or printed on substrate.

Example 5

Indicator Ink Composition Formulation D

An indicator ink composition was formulated by mixing the following ingredients into a dispersion;

| | |
|---|---|
| 36.6% | Purified Water |
| 33.4% | BKUA-2370 Phenol-Formaldehyde Resin |
| 10.2% | E-3358 Polyamide Curing Agent |
| 9.2% | Titanium Dioxide |
| 3.6% | Thickener (associative) |
| 3.0% | Dowanol PNP |
| 1.1% | Citric Acid |
| 1.1% | Sodium Laurel Sulfate |
| 1.0% | 2,6-Dinitrophenol |
| 0.5% | Janus Blue |
| 0.3% | Potassium Iodide |

The above fluid composition is a dual steam/ethylene oxide sterilization indicator composition. The composition was printed using a roto-gravure printing press onto coated and uncoated lithographic paper stock, onto coated and uncoated clear polyester and onto a pharmaceutical lithographic substrate. Viscosity was measured in a number 3 Zahn cup. At 27 seconds the viscosity was 850 cps. When the printed indicators were exposed to the three parameters ISO defines for a steam sterilization process indicator they passed all the requirements and displayed an initial color of blue and a signal color of violet.

These printed indicators also satisfied ISO specifications for an ethylene oxide sterilization process indicator. During the Humidity Dwell, the indicators remained their initial blue color. Following exposure to condition of the Lower Window, the indicators again remained their initial color of blue. Following exposure to the conditions of the Upper Window, the indicators underwent transition to a green signal color. This demonstrates the possibility of a formulation of a dual steam/ethylene oxide indicator composition capable of responding in different ways to different sterilization cycles. The distinctive endpoints associated with each sterilization process can be used to differentiate the specific process to which the sterilization indicator had been exposed. Furthermore, the sensitivity of the indicator to either the steam or the ethylene oxide sterilization cycle can be altered to meet performance objectives associated with each different sterilization process.

Other embodiments and uses of the invention will be apparent to those skilled in the art from consideration of the specification and practice of the invention disclosed herein. The specification and examples should be considered exemplary only with the true scope and spirit of the invention indicated by the following claims.

We claim:

1. An indicator ink comprising a dispersion of phenol-formaldehyde resin in water, at least one colorant and between about 0.5% to about 13% of the total weight of the composition a polyamide curing agent with an amine value between about 100 to about 400.

2. The indicator ink of claim 1 which has a thermotropic property.

3. The indicator ink of claim 2 wherein the thermotropic property is adjustable by altering the concentration of the polyamide curing agent in relation to the concentration of the phenol-formaldehyde resin.

4. The indicator ink of claim 1 wherein the phenol-formaldehyde resin is stabilized with a coating.

5. The indicator ink of claim 4 wherein the coating is a non-ionic colloid.

6. The indicator ink of claim 5 wherein the non-ionic colloid is a polyvinyl alcohol or a polyvinyl acrylic.

7. The indicator ink of claim 1 wherein the phenol-formaldehyde resin has a molecular weight of less than about 1000.

8. The indicator ink of claim 1 wherein the phenol-formaldehyde resin is cross-linked on exposure to a temperature of greater than about 150° C.

9. The indicator ink of claim 1 wherein the phenol-formaldehyde resin is an alkaline catalyzed phenolic resin.

10. The indicator ink of claim 1 wherein the at least one colorant is present at between about 0.5% to about 5% of the total weight of the composition.

11. The indicator ink of claim 1 wherein the at least one colorant comprises one or more dyes selected from the group consisting of reactive dyes and extractable dyes.

12. The indicator ink of claim 11 wherein the reactive dye is selected from the group consisting of substituted phenazines, diazotized products of safranine and quinine oximes.

13. The indicator ink of claim 11 wherein the extractable dye is selected from the group consisting of aniline dyes, sodium sulfonate salts of triphenyl methane dyes and sodium sulfonate salts of induline.

14. The indicator ink of claim 1 further comprising a non-extractable dye.

15. The indicator ink of claim 14 wherein the non-extractable dye is a phenylsafranine dye.

16. The indicator ink of claim 1 further comprising one or more ingredients selected from the group consisting of electrolytes, defoaming agents, dispersing agents, drying agents, opacifiers, rheology modifiers, slip additives, surfactants and viscosity increasing agents.

17. The indicator ink of claim 16 wherein the surfactant is sodium lauryl sulfate.

18. A thermotropic indicator ink comprising a dispersion of phenol-formaldehyde resin in water, at least one colorant and between about 0.5% to about 13% of the total weight of the composition a polyamide curing agent with an amine value between about 100 to about 400 wherein said resin has a molecular weight of less than 1000.

19. The indicator ink of claim 18 wherein the thermotropic property of said ink is adjustable by altering the concentration of the polyamide curing agent in relation to the concentration of the phenol-formaldehyde resin.

20. The indicator ink of claim 18 wherein the phenol-formaldehyde resin is stabilized with a coating.

21. The indicator ink of claim 18 wherein the phenol-formaldehyde resin is cross-linked on exposure to a temperature of greater than about 150° C.

22. The indicator ink of claim 18 wherein the phenol-formaldehyde resin is an alkaline catalyzed phenolic resin.

23. The indicator ink of claim 18 wherein the at least one colorant is present at between about 0.5% to about 5% of the total weight of the composition.

* * * * *